United States Patent
Bedingham et al.

(10) Patent No.: US 8,003,051 B2
(45) Date of Patent: *Aug. 23, 2011

(54) THERMAL STRUCTURE FOR SAMPLE PROCESSING SYSTEMS

(75) Inventors: William Bedingham, Woodbury, MN (US); James E. Aysta, Stillwater, MN (US); Barry W. Robole, Woodville, WI (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/491,959

(22) Filed: Jun. 25, 2009

(65) Prior Publication Data

US 2009/0263280 A1    Oct. 22, 2009

Related U.S. Application Data (63) Continuation of application No. 11/082,374, filed on Mar. 16, 2005, now Pat. No. 7,569,186, which is a continuation of application No. 10/034,993, filed on Dec. 28, 2001, now Pat. No. 6,889,468.

(51) Int. Cl.
*G01N 35/00* (2006.01)
*F27D 11/12* (2006.01)

(52) U.S. Cl. ......... 422/64; 219/428; 219/429; 219/432; 219/435; 422/63; 422/72; 422/104; 436/45

(58) Field of Classification Search ............ 219/388, 219/428–429, 432, 435; 422/63–64, 67, 422/72, 102, 104; 436/45

See application file for complete search history.

(56) References Cited

U.S. PATENT DOCUMENTS

| | | | |
|---|---|---|---|
| 3,555,284 A | | 1/1971 | Anderson |
| 3,713,124 A | * | 1/1973 | Durland et al. .......... 340/870.17 |
| 3,795,451 A | | 3/1974 | Mailen |
| 3,798,459 A | | 3/1974 | Anderson et al. |
| 3,856,470 A | | 12/1974 | Cullis et al. |
| 3,873,217 A | | 3/1975 | Anderson et al. |
| 3,912,799 A | | 10/1975 | Chisholm |
| 3,964,867 A | | 6/1976 | Berry |
| 4,030,834 A | | 6/1977 | Bauer et al. |
| 4,046,511 A | | 9/1977 | Stabile |
| 4,111,304 A | | 9/1978 | Lucas |
| 4,123,173 A | | 10/1978 | Bullock et al. |
| 4,244,916 A | | 1/1981 | Guigan |
| 4,252,538 A | | 2/1981 | Barr |

(Continued)

FOREIGN PATENT DOCUMENTS

CA   2 130 013   3/1999

(Continued)

OTHER PUBLICATIONS

Chiou, J. et al, Analytical Chemistry 2001, 73, 2018-2021.*

(Continued)

*Primary Examiner* — Arlen Soderquist
(74) *Attorney, Agent, or Firm* — Nicole J. Einerson (57) ABSTRACT

Sample processing systems for processing sample materials located in sample processing devices that are separate from the system are disclosed. The sample processing systems include a rotating base plate with raised and/or non-planar thermal structures on which the sample processing devices are located during operation of the systems. The systems may also include structure to urge the sample processing devices against the base plate and thermal structures.

9 Claims, 6 Drawing Sheets

U.S. PATENT DOCUMENTS

| | | | |
|---|---|---|---|
| 4,256,696 A | 3/1981 | Soodak | |
| 4,298,570 A | 11/1981 | Lillig et al. | |
| 4,384,193 A * | 5/1983 | Kledzik et al. | 219/521 |
| 4,390,499 A | 6/1983 | Curtis et al. | |
| 4,396,579 A | 8/1983 | Schroeder et al. | |
| D271,993 S | 12/1983 | Swartz | |
| 4,456,581 A | 6/1984 | Edelmann et al. | |
| D274,553 S | 7/1984 | Perry | |
| 4,476,733 A * | 10/1984 | Chlosta et al. | 73/863.91 |
| 4,488,810 A * | 12/1984 | Hatanaka et al. | 356/244 |
| 4,498,896 A | 2/1985 | Leis | |
| D277,891 S | 3/1985 | Uffenheimer et al. | |
| 4,554,436 A * | 11/1985 | Chlosta et al. | 219/385 |
| 4,580,896 A | 4/1986 | Brickus et al. | |
| 4,632,908 A | 12/1986 | Schultz | |
| D288,124 S | 2/1987 | Brickus et al. | |
| 4,673,657 A | 6/1987 | Christian | |
| 4,695,430 A * | 9/1987 | Coville et al. | 422/65 |
| 4,814,279 A | 3/1989 | Sugaya | |
| 4,839,296 A | 6/1989 | Kennedy et al. | |
| 4,906,432 A | 3/1990 | Geiselman | |
| 4,933,146 A | 6/1990 | Meyer et al. | |
| 4,981,801 A | 1/1991 | Suzuki et al. | |
| 4,990,075 A * | 2/1991 | Wogoman | 422/58 |
| 5,049,591 A | 9/1991 | Hayashi et al. | |
| 5,079,155 A | 1/1992 | Cox et al. | |
| 5,086,337 A | 2/1992 | Noro et al. | |
| 5,128,197 A | 7/1992 | Kobayashi et al. | |
| 5,135,786 A | 8/1992 | Hayashi et al. | |
| 5,139,832 A | 8/1992 | Hayashi et al. | |
| D329,024 S | 9/1992 | Marks | |
| 5,145,935 A | 9/1992 | Hayashi | |
| 5,149,505 A | 9/1992 | English et al. | |
| 5,154,888 A | 10/1992 | Zander et al. | |
| 5,182,083 A | 1/1993 | Barker et al. | |
| 5,207,987 A | 5/1993 | Kureshy et al. | |
| 5,219,526 A | 6/1993 | Long | |
| 5,229,297 A | 7/1993 | Schnipelsky et al. | |
| 5,254,479 A | 10/1993 | Chemelli | |
| 5,258,163 A | 11/1993 | Krause et al. | |
| 5,264,184 A | 11/1993 | Aysta et al. | |
| 5,278,377 A | 1/1994 | Tsai | |
| 5,281,516 A * | 1/1994 | Stapleton et al. | 435/3 |
| 5,288,463 A | 2/1994 | Chemelli | |
| 5,310,523 A | 5/1994 | Smethers et al. | |
| 5,336,467 A | 8/1994 | Heidt et al. | |
| 5,411,065 A | 5/1995 | Meador et al. | |
| 5,415,839 A | 5/1995 | Zaun et al. | |
| 5,422,271 A | 6/1995 | Chen et al. | |
| 5,429,810 A | 7/1995 | Knaepler et al. | |
| 5,438,128 A | 8/1995 | Nieuwkerk et al. | |
| 5,439,649 A * | 8/1995 | Tseung et al. | 422/99 |
| 5,446,270 A | 8/1995 | Chamberlain et al. | |
| 5,460,780 A * | 10/1995 | Devaney et al. | 422/99 |
| 5,461,134 A | 10/1995 | Leir et al. | |
| 5,464,541 A | 11/1995 | Aysta et al. | |
| 5,496,518 A | 3/1996 | Arai et al. | |
| 5,496,520 A | 3/1996 | Kelton et al. | |
| 5,527,931 A | 6/1996 | Rich et al. | |
| 5,529,708 A | 6/1996 | Palmgren et al. | |
| 5,571,410 A | 11/1996 | Swedberg et al. | |
| 5,578,270 A * | 11/1996 | Reichler et al. | 422/67 |
| 5,587,128 A | 12/1996 | Wilding et al. | |
| 5,593,838 A | 1/1997 | Zanzucchi et al. | |
| 5,599,501 A | 2/1997 | Carey et al. | |
| 5,601,141 A * | 2/1997 | Gordon et al. | 165/263 |
| 5,604,130 A | 2/1997 | Warner et al. | |
| 5,616,301 A | 4/1997 | Moser et al. | |
| 5,637,469 A | 6/1997 | Wilding et al. | |
| 5,639,428 A | 6/1997 | Cottingham | |
| 5,639,810 A | 6/1997 | Smith, III et al. | |
| 5,691,208 A | 11/1997 | Miltenyi et al. | |
| RE35,716 E * | 1/1998 | Stapleton et al. | 435/3 |
| 5,720,923 A | 2/1998 | Haff et al. | |
| 5,721,123 A | 2/1998 | Hayes et al. | |
| 5,726,026 A | 3/1998 | Wilding et al. | |
| 5,792,372 A | 8/1998 | Brown et al. | |
| 5,795,547 A | 8/1998 | Moser et al. | |
| 5,800,785 A | 9/1998 | Bochner et al. | |
| 5,804,141 A | 9/1998 | Chianese | |
| 5,811,296 A | 9/1998 | Chemelli et al. | |
| 5,819,842 A | 10/1998 | Potter et al. | |
| 5,822,903 A | 10/1998 | Davis, Sr. | |
| 5,833,923 A | 11/1998 | McClintock et al. | |
| 5,856,194 A | 1/1999 | Arnquist et al. | |
| 5,863,502 A | 1/1999 | Southgate et al. | |
| 5,863,801 A | 1/1999 | Southgate et al. | |
| 5,869,002 A | 2/1999 | Limon et al. | |
| 5,876,675 A | 3/1999 | Kennedy | |
| 5,886,863 A | 3/1999 | Nagasaki et al. | |
| 5,922,617 A | 7/1999 | Wang et al. | |
| 5,925,455 A | 7/1999 | Bruzzone et al. | |
| 5,948,227 A | 9/1999 | Dubrow | |
| 5,976,468 A | 11/1999 | Godec et al. | |
| 5,997,818 A | 12/1999 | Hacker et al. | |
| 6,001,643 A | 12/1999 | Spaulding | |
| 6,007,690 A | 12/1999 | Nelson et al. | |
| 6,007,914 A | 12/1999 | Joseph et al. | |
| 6,013,513 A | 1/2000 | Reber et al. | |
| 6,030,581 A | 2/2000 | Virtanen | |
| 6,048,457 A | 4/2000 | Kopaciewicz et al. | |
| 6,063,589 A | 5/2000 | Kellogg et al. | |
| 6,068,751 A | 5/2000 | Neukermans | |
| 6,074,827 A | 6/2000 | Nelson et al. | |
| 6,093,370 A | 7/2000 | Yasuda et al. | |
| 6,103,199 A | 8/2000 | Bjornson et al. | |
| 6,143,247 A | 11/2000 | Sheppard, Jr. et al. | |
| 6,143,248 A | 11/2000 | Kellogg et al. | |
| 6,153,012 A | 11/2000 | Rupp et al. | |
| 6,168,759 B1 * | 1/2001 | Green et al. | 422/64 |
| 6,168,948 B1 | 1/2001 | Anderson et al. | |
| 6,183,693 B1 * | 2/2001 | Bogen et al. | 422/64 |
| 6,184,029 B1 | 2/2001 | Wilding et al. | |
| 6,190,617 B1 | 2/2001 | Clark et al. | |
| 6,197,595 B1 | 3/2001 | Anderson et al. | |
| 6,200,474 B1 | 3/2001 | Kopaciewicz et al. | |
| D441,873 S | 5/2001 | Köhler | |
| 6,265,168 B1 | 7/2001 | Gjerde et al. | |
| 6,284,113 B1 | 9/2001 | Bjornson et al. | |
| 6,296,809 B1 * | 10/2001 | Richards et al. | 422/64 |
| 6,302,134 B1 | 10/2001 | Kellogg et al. | |
| 6,306,273 B1 | 10/2001 | Wainright et al. | |
| 6,319,469 B1 | 11/2001 | Mian et al. | |
| 6,344,326 B1 | 2/2002 | Nelson et al. | |
| 6,375,898 B1 | 4/2002 | Ulrich | |
| 6,391,264 B2 | 5/2002 | Hammer et al. | |
| 6,399,025 B1 | 6/2002 | Chow | |
| 6,413,782 B1 | 7/2002 | Parce et al. | |
| 6,432,365 B1 | 8/2002 | Levin et al. | |
| 6,440,725 B1 | 8/2002 | Pourahmadi et al. | |
| 6,450,047 B2 | 9/2002 | Swedberg et al. | |
| 6,451,260 B1 | 9/2002 | Düsterhöft et al. | |
| 6,461,287 B1 | 10/2002 | Glater | |
| 6,465,225 B1 | 10/2002 | Fuhr et al. | |
| 6,467,275 B1 | 10/2002 | Ghosal | |
| 6,479,300 B1 | 11/2002 | Jiang et al. | |
| 6,527,432 B2 | 3/2003 | Kellogg et al. | |
| 6,532,997 B1 | 3/2003 | Bedingham et al. | |
| 6,548,788 B2 | 4/2003 | Kellogg et al. | |
| 6,558,947 B1 | 5/2003 | Lund et al. | |
| 6,565,808 B2 | 5/2003 | Hudak et al. | |
| 6,566,637 B1 | 5/2003 | Revesz et al. | |
| 6,572,830 B1 | 6/2003 | Burdon et al. | |
| 6,582,662 B1 | 6/2003 | Kellogg et al. | |
| 6,593,143 B1 | 7/2003 | Gordon | |
| 6,617,136 B2 | 9/2003 | Parthasarathy et al. | |
| 6,627,159 B1 | 9/2003 | Bedingham et al. | |
| 6,632,399 B1 | 10/2003 | Kellogg et al. | |
| 6,645,758 B1 | 11/2003 | Schnipelsky et al. | |
| 6,648,853 B1 | 11/2003 | McEntee | |
| 6,660,147 B1 | 12/2003 | Woudenberg et al. | |
| 6,664,104 B2 | 12/2003 | Pourahmadi et al. | |
| 6,692,596 B2 | 2/2004 | Moll et al. | |
| 6,706,519 B1 * | 3/2004 | Kellogg et al. | 435/287.2 |
| 6,720,187 B2 | 4/2004 | Bedingham et al. | |
| 6,723,236 B2 | 4/2004 | Fisk et al. | |
| 6,730,516 B2 | 5/2004 | Jedrzejewski et al. | |

| | | | |
|---|---|---|---|
| 6,734,401 B2 | 5/2004 | Bedingham et al. | |
| 6,780,818 B2 | 8/2004 | Gundel et al. | |
| 6,814,935 B2 | 11/2004 | Harms et al. | |
| 6,824,738 B1 | 11/2004 | Neeper et al. | |
| 6,889,468 B2 | 5/2005 | Bedingham et al. | |
| 6,987,253 B2 | 1/2006 | Bedingham et al. | |
| 7,026,168 B2 | 4/2006 | Bedingham et al. | |
| 7,164,107 B2 | 1/2007 | Bedingham et al. | |
| 7,192,560 B2 | 3/2007 | Parthasarathy et al. | |
| 7,273,591 B2 | 9/2007 | Sellers et al. | |
| 7,322,254 B2 | 1/2008 | Bedingham et al. | |
| 7,323,660 B2 | 1/2008 | Bedingham et al. | |
| 7,332,326 B1* | 2/2008 | Kellogg et al. | 435/287.2 |
| D564,667 S | 3/2008 | Bedingham et al. | |
| 7,396,508 B1* | 7/2008 | Richards et al. | 422/64 |
| 7,435,933 B2 | 10/2008 | Bedingham et al. | |
| 7,494,770 B2 | 2/2009 | Wilding et al. | |
| 7,569,186 B2* | 8/2009 | Bedingham et al. | 422/63 |
| 2001/0045000 A1 | 11/2001 | Gundel et al. | |
| 2002/0047003 A1 | 4/2002 | Bedingham et al. | |
| 2002/0048533 A1 | 4/2002 | Harms et al. | |
| 2002/0064885 A1 | 5/2002 | Bedingham et al. | |
| 2002/0097632 A1* | 7/2002 | Kellogg et al. | 366/220 |
| 2003/0013203 A1 | 1/2003 | Jedrzejewski et al. | |
| 2003/0017567 A1 | 1/2003 | Parthasarathy et al. | |
| 2003/0044322 A1 | 3/2003 | Andersson et al. | |
| 2003/0053934 A1 | 3/2003 | Andersson et al. | |
| 2003/0118804 A1 | 6/2003 | Bedingham et al. | |
| 2003/0120062 A1 | 6/2003 | Parthasarathy et al. | |
| 2003/0138779 A1 | 7/2003 | Parthasarathy et al. | |
| 2003/0139550 A1 | 7/2003 | Savu et al. | |
| 2003/0152491 A1 | 8/2003 | Kellogg et al. | |
| 2003/0152994 A1 | 8/2003 | Woudenberg et al. | |
| 2003/0155034 A1 | 8/2003 | De Beukeleer et al. | |
| 2003/0228706 A1 | 12/2003 | Ramstad et al. | |
| 2003/0231878 A1 | 12/2003 | Shigeura | |
| 2004/0016702 A1 | 1/2004 | Hennessy et al. | |
| 2004/0016898 A1 | 1/2004 | Cox et al. | |
| 2004/0018116 A1 | 1/2004 | Desmond et al. | |
| 2004/0018117 A1 | 1/2004 | Desmond et al. | |
| 2004/0023371 A1 | 2/2004 | Fawcett | |
| 2004/0121471 A1 | 6/2004 | Dufresne et al. | |
| 2004/0179974 A1 | 9/2004 | Bedingham et al. | |
| 2004/0209258 A1 | 10/2004 | Parthasarathy et al. | |
| 2005/0028587 A1* | 2/2005 | Baer et al. | 73/204.26 |
| 2005/0036911 A1 | 2/2005 | Sellers et al. | |
| 2005/0130177 A1 | 6/2005 | Bedingham et al. | |
| 2005/0142563 A1 | 6/2005 | Haddad et al. | |
| 2005/0142570 A1 | 6/2005 | Parthasarathy et al. | |
| 2005/0142571 A1 | 6/2005 | Parthasarathy et al. | |
| 2005/0142663 A1 | 6/2005 | Parthasarathy et al. | |
| 2005/0180890 A1 | 8/2005 | Bedingham et al. | |
| 2006/0013732 A1 | 1/2006 | Parthasarathy et al. | |
| 2006/0269451 A1 | 11/2006 | Bedingham et al. | |
| 2007/0009391 A1 | 1/2007 | Bedingham et al. | |
| 2007/0010007 A1 | 1/2007 | Aysta et al. | |
| 2007/0114229 A1 | 5/2007 | Bedingham et al. | |
| 2007/0142780 A1 | 6/2007 | Van Lue | |
| 2009/0263280 A1 | 10/2009 | Bedingham et al. | |

FOREIGN PATENT DOCUMENTS

| | | |
|---|---|---|
| DE | 37 12 624 A1 | 11/1988 |
| EP | 0 169 306 A2 | 1/1986 |
| EP | 0 281 368 | 9/1988 |
| EP | 0 169 306 | 5/1990 |
| EP | 0 807 468 | 8/1994 |
| EP | 0 402 994 | 11/1994 |
| EP | 0 693 560 A2 | 1/1996 |
| EP | 0 693 560 A3 | 1/1996 |
| EP | 0 965 388 | 12/1999 |
| EP | 1 010 979 | 6/2000 |
| EP | 0 807 486 | 12/2001 |
| EP | 0 810 030 B1 | 3/2003 |
| JP | 60-57259 | 4/1985 |
| JP | 9-72912 | 3/1997 |
| JP | 11124419 | 5/1999 |
| WO | WO 91/19567 | 12/1991 |
| WO | WO 94/26414 | 11/1994 |
| WO | WO 94/29400 | 12/1994 |
| WO | WO 95/18676 A1 | 7/1995 |
| WO | WO 95/19781 | 7/1995 |
| WO | WO 96/15576 | 5/1996 |
| WO | WO 96/34028 A1 | 10/1996 |
| WO | WO 96/34029 A1 | 10/1996 |
| WO | WO 96/35458 A2 | 11/1996 |
| WO | WO 96/41864 A1 | 12/1996 |
| WO | WO 97/00230 | 1/1997 |
| WO | WO 97/19567 | 5/1997 |
| WO | WO 97/21090 A1 | 6/1997 |
| WO | WO 97/46707 A2 | 12/1997 |
| WO | WO 98/04909 | 2/1998 |
| WO | WO 98/07019 A1 | 2/1998 |
| WO | WO 98/49340 A1 | 11/1998 |
| WO | WO 98/50147 A1 | 11/1998 |
| WO | WO 98/53311 A2 | 11/1998 |
| WO | WO 99/09394 A1 | 2/1999 |
| WO | WO 99/15876 | 4/1999 |
| WO | WO 99/15888 | 4/1999 |
| WO | WO 99/40174 | 8/1999 |
| WO | WO 99/44740 | 9/1999 |
| WO | WO 99/46591 | 9/1999 |
| WO | WO 99/55827 A1 | 11/1999 |
| WO | WO 99/58245 A1 | 11/1999 |
| WO | WO 99/67639 A1 | 12/1999 |
| WO | WO 00/05582 | 2/2000 |
| WO | WO 00/40750 A1 | 7/2000 |
| WO | WO 00/45180 | 8/2000 |
| WO | WO 00/50172 A1 | 8/2000 |
| WO | WO 00/50642 A1 | 8/2000 |
| WO | WO 00/62051 | 10/2000 |
| WO | WO 00/68336 A1 | 11/2000 |
| WO | WO 00/69560 A1 | 11/2000 |
| WO | WO 00/78455 A1 | 12/2000 |
| WO | WO 00/79285 A2 | 12/2000 |
| WO | WO 00/79285 A3 | 12/2000 |
| WO | WO 01/07892 | 2/2001 |
| WO | WO 01/12327 | 2/2001 |
| WO | WO 01/30995 | 5/2001 |
| WO | WO 01/38865 | 5/2001 |
| WO | WO 03/054509 | 7/2003 |
| WO | WO 03/054510 | 7/2003 |
| WO | WO 03/058224 | 7/2003 |
| WO | WO 03/058253 | 7/2003 |
| WO | WO 03/104783 A1 | 12/2003 |
| WO | WO 2004/010760 | 2/2004 |
| WO | WO 2004/011142 | 2/2004 |
| WO | WO 2004/011143 A2 | 2/2004 |
| WO | WO 2004/011143 A3 | 2/2004 |
| WO | WO 2004/011147 A1 | 2/2004 |
| WO | WO 2004/011148 | 2/2004 |
| WO | WO 2004/011149 | 2/2004 |
| WO | WO 2004/011365 | 2/2004 |
| WO | WO 2004/011592 | 2/2004 |
| WO | WO 2004/011681 A1 | 2/2004 |
| WO | WO 2004/094672 | 11/2004 |
| WO | WO 2005/005045 | 1/2005 |
| WO | WO 2005/016532 | 2/2005 |

OTHER PUBLICATIONS

*Handbook of Pressure Sensitive Adhesive Technology*, Donatas Satas (Ed.) $2^{nd}$ Edition, p. 172, and FIG. 8-16 on p. 173, Van Nostrand Reinhold, New York, NY 1989.
*Handbook of Pressure Sensitive Adhesive Technology*, $3^{rd}$ Edition, pp. 508-517.
Litton Product Brochure; Poly Scientific EC3848 High Speed Slip Ring Capsule; Blacksburg, VA; 2 pgs (Oct. 1999).
Meridian Laboratory Datasheet [online]; Rotocon high performance rotary electrical contacts; 3 pgs [retrieved on Jun. 18, 2002]. Retrieved from the Internet; <http://www.meridianlab.com/>.
Meridian Laboratory Datasheet [online]; Model MM Micro-Minature; 3 pgs [retrieved on Jul. 19, 2001]. Retrieved from the Internet: <http://www.meridianlab.com/mm.htm>.
Motion Technology Product Guide; Commercial and Military/Aerospace Applications; Blacksburg, VA; 8 pgs (Jul. 1999).
NIST Grant, Project Brief [online]; "Tools for DNA Diagnostics (Oct. 1998) Integrated, Micro-Sample Preparation System for Genetic Analysis," [retrieved on Aug. 5, 2002] 2 pgs. Retrieved from the internet at <http://jazz.nist.gov/atpcf/prjbriefs/prjbrief.cfm?ProjectNumber=98-08-0031>.

Emmer, A. et al.; "Wall deactivation with fluorosurfactants for capillary electrophoretic analysis of biomolecules"; Electrophoresis 2001, 22; pp. 660-665.

Garcia, A. et al.; "Comparison of Two Leukocyte Extraction Methods for Cytomegalovirus Antigenemia Assay"; Journal of Clinical Microbiology, Jan. 1996; vol. 34, No. 1; pp. 182-184.

* cited by examiner

THERMAL STRUCTURE FOR SAMPLE PROCESSING SYSTEMS

RELATED APPLICATIONS

This is a continuation of U.S. patent application Ser. No. 11/082,374 filed Mar. 16, 2005 titled SYSTEMS FOR USING SAMPLE PROCESSING DEVICES, now U.S. Pat. No. 7,569,186, which is a continuation of U.S. patent application Ser. No. 10/034,993 filed on Dec. 28, 2001 titled MODULAR SYSTEMS AND METHODS FOR USING SAMPLE PROCESSING DEVICES, now U.S. Pat. No. 6,889,468, both of which are incorporated herein by reference in their entirety.

GRANT INFORMATION

The present invention may have been made with support from the U.S. Government under NIST Grant No. 70NANB8H4002. The U.S. Government may have certain rights to the inventions recited herein.

TECHNICAL FIELD

The present invention relates to systems and methods for using rotating sample processing devices to, e.g., amplify genetic materials, etc.

BACKGROUND

Many different chemical, biochemical, and other reactions are sensitive to temperature variations. Examples of thermal processes in the area of genetic amplification include, but are not limited to, Polymerase Chain Reaction (PCR), Sanger sequencing, etc. One approach to reducing the time and cost of thermally processing multiple samples is to use a device including multiple chambers in which different portions of one sample or different samples can be processed simultaneously. Examples of some reactions that may require accurate chamber-to-chamber temperature control, comparable temperature transition rates, and/or rapid transitions between temperatures include, e.g., the manipulation of nucleic acid samples to assist in the deciphering of the genetic code. Nucleic acid manipulation techniques include amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR). Other examples of nucleic acid manipulation techniques include, e.g., Sanger sequencing, ligand-binding assays, etc.

Systems designed to process sample materials using these techniques are typically complex and expensive. Furthermore, many of the sample processing systems are not particularly flexible in adapting to different sample processing devices. The use of different sample processing devices may, however, be required when different types of sample or different protocols are to be used.

For example, a typical sample processing device (e.g., thermal cycler, sequencing machine, etc.) can perform only one function on sample materials that have certain properties or characteristics. Furthermore, the output of such devices must be transferred to another device if additional processing is desired. Such transfers may be robotically or manually, and both may allow for the introduction of errors such as mislabeling, cross-contamination, etc.

SUMMARY OF THE INVENTION

The present invention provides sample processing systems and methods of using those systems for processing sample materials located in devices that are separate from the system. The sample processing systems include a rotating base plate on which the sample processing devices are located during operation of the systems.

In one aspect, the present invention provides a sample processing system that includes a base plate adapted to receive a sample processing device proximate a top surface of the base plate; a thermal structure exposed on the top surface of the base plate, wherein an upper surface of the thermal structure contacts a sample processing device received proximate the top surface of the base plate, and wherein the upper surface of the thermal structure is raised relative to the top surface of the base plate adjacent the thermal structure; a drive system adapted to rotate the base plate about an axis of rotation; and an electromagnetic energy source adapted to direct electromagnetic energy at the thermal structure while the base plate is rotating about the axis of rotation.

In another aspect, the present invention provides a sample processing system that includes a base plate adapted to receive a sample processing device proximate a top surface of the base plate; a thermal structure exposed on the top surface of the base plate, wherein an upper surface of the thermal structure contacts a sample processing device received proximate the top surface of the base plate, and wherein the upper surface of the thermal structure is raised relative to the top surface of the base plate adjacent the thermal structure, and wherein the thermal structure includes shoulders that set the upper surface of the thermal structure off from the top surface of the base plate adjacent the thermal structure, and wherein the thermal structure includes at least one raised protrusion that extends above the surrounding portions of the upper surface of the thermal structure, and still further wherein the thermal structure includes a lower surface that is exposed proximate a bottom surface of the base plate; a drive system adapted to rotate the base plate about an axis of rotation; and an electromagnetic energy source adapted to direct electromagnetic energy at the thermal structure while the base plate is rotating about the axis of rotation.

In another aspect, the present invention provides a sample processing system that includes a base plate adapted to receive a sample processing device proximate a top surface of the base plate; a thermal structure exposed on the top surface of the base plate, wherein the thermal structure includes a non-planar upper surface; a drive system adapted to rotate the base plate about an axis of rotation; and an electromagnetic energy source adapted to direct electromagnetic energy at the thermal structure while the base plate is rotating about the axis of rotation.

In another aspect, the present invention provides a sample processing system that includes a base plate adapted to receive a sample processing device proximate a top surface of the base plate; a thermal structure exposed on the top surface of the base plate, wherein the thermal structure includes an upper surface that contacts a sample processing device received proximate the top surface of the base plate; means for urging a sample processing device towards the top surface of the base plate, wherein the sample processing device is forced against the upper surface of the thermal structure; a drive system adapted to rotate the base plate about an axis of rotation; an electromagnetic energy source adapted to direct electromagnetic energy at the thermal structure while the base plate is rotating about the axis of rotation.

In another aspect, the present invention provides a sample processing system that includes a base plate adapted to receive a sample processing device proximate a top surface of the base plate; a thermal structure exposed on the top surface of the base plate, wherein the thermal structure includes an upper surface that contacts a sample processing device received proximate the top surface of the base plate; a drive system adapted to rotate the base plate about an axis of rotation; a platen adapted to force a sample processing device against the upper surface of the thermal structure; and an electromagnetic energy source adapted to direct electromagnetic energy at the thermal structure while the base plate is rotating about the axis of rotation.

In another aspect, the present invention provides a sample processing system that includes a base plate adapted to receive a sample processing device proximate a top surface of the base plate; a thermal structure exposed on the top surface of the base plate, wherein the thermal structure includes an upper surface that contacts a sample processing device received proximate the top surface of the base plate; a drive system adapted to rotate the base plate about an axis of rotation; a spindle that extends through a central opening in a sample processing device, the spindle adapted to draw the sample processing device towards the top surface of the base plate; and an electromagnetic energy source adapted to direct electromagnetic energy at the thermal structure while the base plate is rotating about the axis of rotation.

These and other features and advantages of the devices, systems and methods of the invention are described below with respect to illustrative embodiments of the invention.

As used in connection with the present invention, the term "electromagnetic energy" (and variations thereof) means electromagnetic energy (regardless of the wavelength/frequency) capable of being delivered from a source to a desired location or material in the absence of physical contact. Non-limiting examples of electromagnetic energy include laser energy, radio-frequency (RF), microwave radiation, light energy (including the ultraviolet through infrared spectrum), etc. It may be preferred that electromagnetic energy be limited to energy falling within the spectrum of ultraviolet to infrared radiation (including the visible spectrum).

DETAILED DESCRIPTION OF ILLUSTRATIVE EMBODIMENTS OF THE INVENTION

The present invention provides methods and systems for sample processing devices that can be used in methods that involve thermal processing, e.g., sensitive chemical processes such as PCR amplification, ligase chain reaction (LCR), self-sustaining sequence replication, enzyme kinetic studies, homogeneous ligand binding assays, and more complex biochemical or other processes that require precise thermal control and/or rapid thermal variations. The sample processing systems are capable of providing simultaneous rotation of the sample processing device in addition to control over the temperature of sample materials in process chambers on the devices.

Some examples of suitable sample processing devices that may be used in connection with the methods and systems of the present invention may be described in, e.g., commonly-assigned U.S. patent application Ser. No. 09/894,810 filed on Jun. 28, 2001 and entitled ENHANCED SAMPLE PROCESSING DEVICES SYSTEMS AND METHODS and U.S. patent application Ser. No. 09/895,010 filed on Jun. 28, 2001 and entitled SAMPLE PROCESSING DEVICES, each of which is hereby incorporated by reference in its entirety. Other useable device constructions may be found in, e.g., U.S. Provisional Patent Application Ser. No. 60/214,508 filed on Jun. 28, 2000 and entitled THERMAL PROCESSING DEVICES AND METHODS; U.S. Provisional Patent Application Ser. No. 60/214,642 filed on Jun. 28, 2000 and entitled SAMPLE PROCESSING DEVICES, SYSTEMS AND METHODS; U.S. Provisional Patent Application Ser. No. 60/237,072 filed on Oct. 2, 2000 and entitled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METHODS; U.S. Provisional Patent Application Ser. No. 60/284,637 filed on Apr. 18, 2001 and titled ENHANCED SAMPLE PROCESSING DEVICES, SYSTEMS AND METHODS; and U.S. patent application Ser. No. 09/895,001 filed Jun. 28, 2001 and entitled SAMPLE PROCESSING DEVICES AND CARRIERS, each of which is hereby incorporated by reference in its entirety. Other potential device constructions may be found in, e.g., U.S. patent application Ser. No. 09/710,184 filed on Nov. 10, 2000 and titled CENTRIFUGAL FILLING OF SAMPLE PROCESSING DEVICES, the entirety of which is hereby incorporated by reference.

The sample processing systems of the present invention include base plates attached to a drive system in manner that provides for rotation of the base plate about an axis of rotation. When a sample processing device is secured to the base plate, the sample processing device is rotated with the base plate. The base plates include at least one thermal structure that can be used to heat portions of the sample processing devices and may include a variety of other components as well, e.g., temperature sensors, resistance heaters, thermoelectric modules, light sources, light detectors, transmitters, receivers, etc.

All of the base plates used and sample processing systems according to the present invention are preferably modularly attached to the drive system that rotates the base plates about an axis of rotation. The use of modular base plates can provide many advantages to sample processing systems such as the ability to quickly and easily replace a malfunctioning base plates, the ability to replace a base plate with one configuration with a base plate having a different configuration, etc.

Although relative positional terms such as "top" and "bottom" may be used in connection with the present invention, it should be understood that those terms are used in their relative sense only. For example, when used in connection with the devices of the present invention, "top" and "bottom" are used to signify opposing sides of the base plates, with the top surface typically located closest to the sample processing device mounted to the base plate during sample processing.

In actual use, elements described as "top" or "bottom" may be found in any orientation or location and should not be considered as limiting the methods, systems, and devices to any particular orientation or location. For example, the top surface of the device may actually be located below the bottom surface of the device in use (although it would still be found on the opposite side of the device from the bottom surface).

Figure 1:
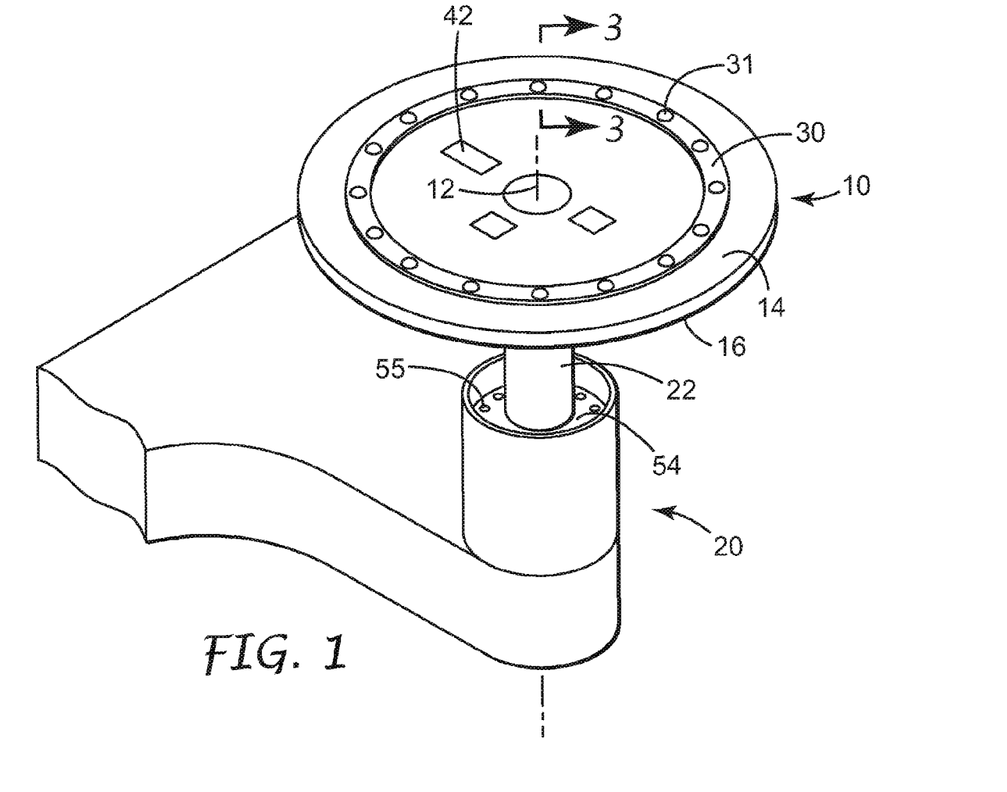
FIG. 1 is a top perspective view of one sample processing system according to the present invention.

One illustrative sample processing system is schematically depicted in FIG. 1. The system includes a base plate 10 that rotates about an axis of rotation 12. The base plate 10 is attached to a drive system 20 through a shaft 22. The shaft 22 is, in the illustrated embodiment, rotated by a belt operably attached to a motor (not shown). It will, however, be understood that the shaft 22 could be coupled to the motor by any suitable alternative mechanism or the shaft 22 may be the output shaft of the motor itself (a direct drive configuration).

The top surface 14 of the depicted base plate 10 includes a thermal structure 30 that is preferably located directly beneath selected portions of a sample processing device attached to the base plate 10 during sample processing. The use of such thermal structures in connection with rotating base plates is described in, e.g., at least some of the patent applications identified above.

Figure 2:
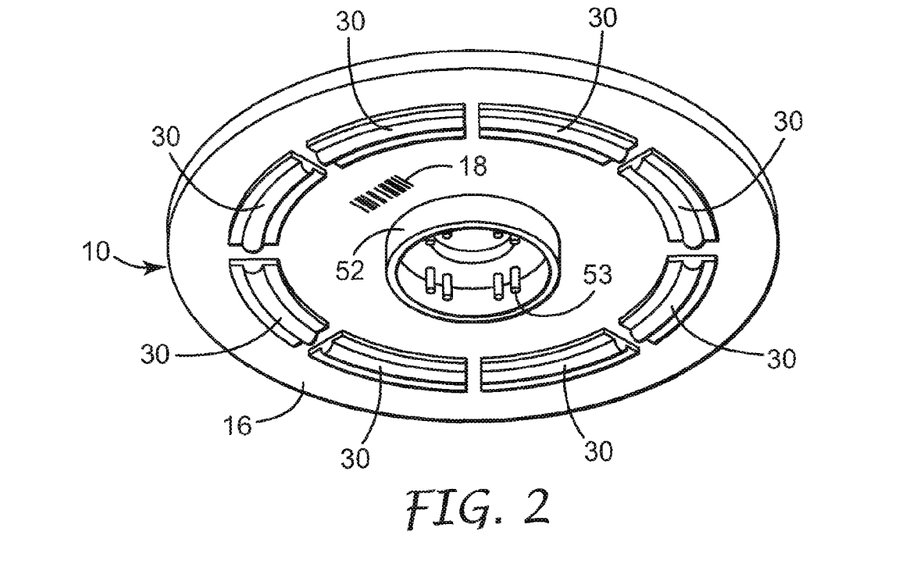
FIG. 2 is a bottom perspective view of the base plate of the sample processing system of FIG. 1, with the base plate removed from the system.
Figure 3:
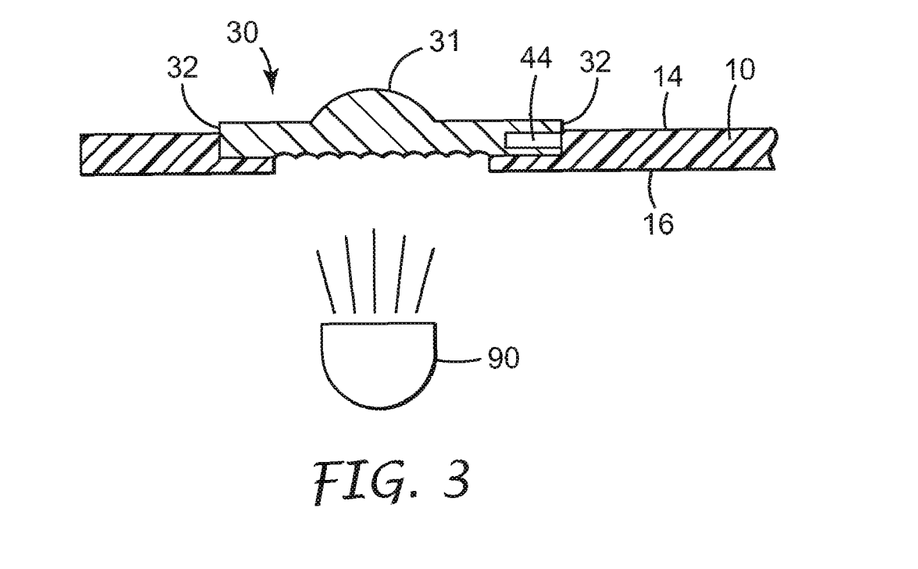
FIG. 3 is an enlarged partial cross-sectional view of the sample processing system of FIG. 1.

FIG. 2 is a perspective view of the bottom 16 of the base plate 10 and FIG. 3 is a cross-sectional view of the base plate 10. The base plate 10 is constructed such that the thermal structure is exposed on both the top and the bottom surfaces 14 and 16. By exposing the thermal structure 30 on the top surface 14 of the base plate 10, a more direct thermal path can be provided between the thermal structure 30 and any sample processing device located on the top surface 14 of the base plate 10.

The thermal structure 30 is also preferably exposed on the bottom surface 16 of the base plate by providing an annular opening in the base plate 10, with the outermost annular portion of the base plate 10 connected to the central portion of the base plate 10 by a series of struts. Exposing the thermal structure 30 on the bottom surface of the base plate 10 may provide an advantage when the thermal structure is to be heated by electromagnetic energy in the form of light.

One example of an electromagnetic energy source 90 is depicted in FIG. 3, with the electromagnetic energy emitted by the source 90 directed towards the bottom surface 16 of the base plate 10. Examples of some suitable electromagnetic energy sources may include, but are not limited to, lasers, broadband electromagnetic energy sources (e.g., white light), etc.

Where the thermal structure 30 is to be heated by a remote energy source, i.e., an energy source that does not deliver thermal energy to the thermal structure by direct contact, the thermal structure 30 is preferably constructed to absorb electromagnetic energy and convert the absorbed electromagnetic energy into thermal energy. The materials used in the thermal structure 30 preferably possess sufficient thermal conductivity and absorb electromagnetic energy generated by the electromagnetic source 90 at sufficient rates. In addition, it may also be desirable that the material or materials used for the thermal structures 30 have sufficient heat capacity to provide a heat capacitance effect. Examples of some suitable materials include, but are not limited to: aluminum, copper, gold, etc. If the thermal structure 30 is constructed of materials that do not, themselves, absorb electromagnetic energy at a sufficient rate, it may be preferred that the thermal structure 30 include a material that improves energy absorption. For example, the thermal structure 30 may be coated with an electromagnetic energy absorptive material such as carbon black, polypyrrole, inks, etc.

In addition to selection of suitable materials for the thermal structure 30, it may also be preferred to include grooves as depicted (or other surface structure) to increase the amount of surface area exposed to the e-m energy emitted by the source 90. Increasing the surface area of the thermal structure 30 exposed to the e-m energy from source 70 may enhance the rate at which energy is absorbed by the thermal structure 30. The increased surface area used in the thermal structures 30 may also increase the efficiency of electromagnetic energy absorption.

It may further be desirable that the thermal structure 30 be relatively thermally isolated from the remainder of the base plate 10 such that only limited amounts (if any) of the thermal energy in the thermal structure 30 is transferred to the remainder of the base plate 10. That thermal isolation may be achieved, for example, by manufacturing the support structure of the base plate 10 of materials that absorb only limited amounts of thermal energy, e.g. polymers, etc. Some suitable materials for the support structure of base plate 10 include, e.g., glass-filled plastics (e.g., polyetheresterketone), silicones, ceramics, etc.

Although the base plate 10 includes a thermal structure 30 in the form of a substantially continuous circular ring, the thermal structures used in base plates of systems according to the present invention may alternatively be provided as a series of discontinuous thermal elements, e.g., circles, squares, located beneath process chambers on a sample processing device (not shown) located on the top surface 14 of the base plate 10. One advantage, however, of a continuous ring thermal structure is that temperature of the thermal structure 30 may equilibrate during heating. If a group of process chambers in a sample processing device are arranged such that they are in direct contact with the thermal structure 30, there is a potential to improve chamber-to-chamber temperature uniformity for all process chambers located above the continuous thermal structure 30.

Although the depicted base plate 10 includes only one thermal structure 30, it will be understood that base plates in the systems of the present invention could include any number of thermal structures that are necessary to transfer thermal energy to or from the selected process chambers in a sample processing device located thereon. Further, it may be preferred that, where more than one thermal structure is provided, the different thermal structures be independent of each other such that no significant amount of thermal energy is transferred between the different independent thermal structures. One example of an alternative in which independent thermal structures are provided may be in the form of concentric annular rings.

Another optional feature of sample processing systems according to the present invention are the raised protrusions 31 that extend above the surrounding surface of the thermal structure 30. The size and location of the protrusions 31 are preferably selected to correspond to the size and location of any process chambers on a sample processing device to be located on the base plate 10.

The protrusions 31 may enhance thermal transfer between the process chambers and base plate 10 in a number of ways. For example, if the protrusions 31 extend at least partially into the process chambers of the sample processing device, they can increase the surface area of the process chamber that is exposed to the thermal structure 30. In addition, by affirmatively engaging any process chambers, the protrusions 31 may reduce or eliminate any air gaps between the process chambers and the thermal structure 30 in the area of the process chambers. Such air gaps may insulate the process chambers from the thermal structure, thereby degrading thermal transfer.

Still another optional feature depicted in FIG. 3 is that the thermal structure 30 itself may be raised relative to the surrounding surface 14 of the base plate 10. In FIG. 3, the thermal structure 30 includes shoulders 32 that set the upper surface of the thermal structure 30 off from the surrounding surface 14 of the base plate 10. A raised thermal structure 30 preferably raises any sample processing device mounted on the base plate 10, such that the sample processing device does not contact the surface 14 of the base plate 10 that surrounds the thermal structure 30. Alternatively, the protrusions 31 alone may be high enough relative to the surrounding surface 14 of the base plate 10 such that the entire upper surface of the thermal structure 30 need not be raised relative to the surrounding surface 14 of the base plate 10 as seen in FIG. 3.

Further, it may be desirable to supply a force on a sample processing device to urge the sample processing device and base plate 10 towards each other. In some embodiments, such a force may be provided by a platen urging the sample processing device against the base plate 10. In other embodiments, the sample processing device may be drawn towards the base plate 10 by, e.g., a spindle that extends through a central opening in the sample processing device and draws the sample processing device towards base plate 10. Other structures and/or mechanisms for providing a force urging a sample processing device and base plate 10 together will be known to those skilled in the art.

The electromagnetic energy source may be in a form that provides electromagnetic energy to only one thermal structure at a time, or it may be capable of heating two or more thermal structures simultaneously. If heating of different thermal structures at different times is desired, a separate electromagnetic energy source dedicated to each thermal structure may be provided and controlled to supply electromagnetic energy as needed. Alternatively, a single energy source may be provided in connection with multiple different thermal structures, with the single energy source being moved or positioned to provide electromagnetic energy that impinges the thermal structure or thermal structures to be heated. In another alternative, a shuttering system may be provided in connection with the energy source such that electromagnetic energy is delivered to the necessary thermal structure or structures as needed. In still another alternative, the electromagnetic energy may be delivered through the use of a reflective delivery system incorporating mirrors, waveguides, optical fibers, or any structure or structures capable of controlling the delivery of electromagnetic energy to the thermal structure or structures on the base plate.

One potential advantage of using absorptive thermal structures in conjunction with the electromagnetic source 90 is that compatibility between the electromagnetic energy source and any reagents or other materials located within the process chambers of a sample processing device located on the top surface 14 of the base plate 10 may be improved. The thermal structures may preferably be opaque to the electromagnetic energy produced by source 90. As a result, materials within the sample processing device may be substantially shielded from direct exposure to the electromagnetic energy that could, in some instances, be detrimental to the desired reactions.

The depicted base plate 10 also includes optional temperature sensors to detect the temperature of the thermal structure 30 during operation of the system. FIG. 1 depicts a reference temperature sensor 42 located within the base plate 10, spaced away from the thermal structure 30. A second temperature sensor 44 is depicted in FIG. 3 embedded within the mass of the thermal structure 30. Data from the two sensors can be used together to accurately measure the temperature of the thermal structure 30 during operation of the system. It will be understood that the reference temperature sensor 42 may not be required in some systems that include a temperature sensor measuring the temperature of the thermal structure 30.

Signals from the sensors 42 and 44 may be used to control the amount of energy provided by the electromagnetic energy source 90 or to control the rate and/or duration of rotation of the base plate 10 as a part of any system control over both heating and cooling of the thermal structure 30. Alternatively, the temperature of the thermal structure 30 may be monitored remotely by, e.g., infrared emissions, etc.

Figure 4:
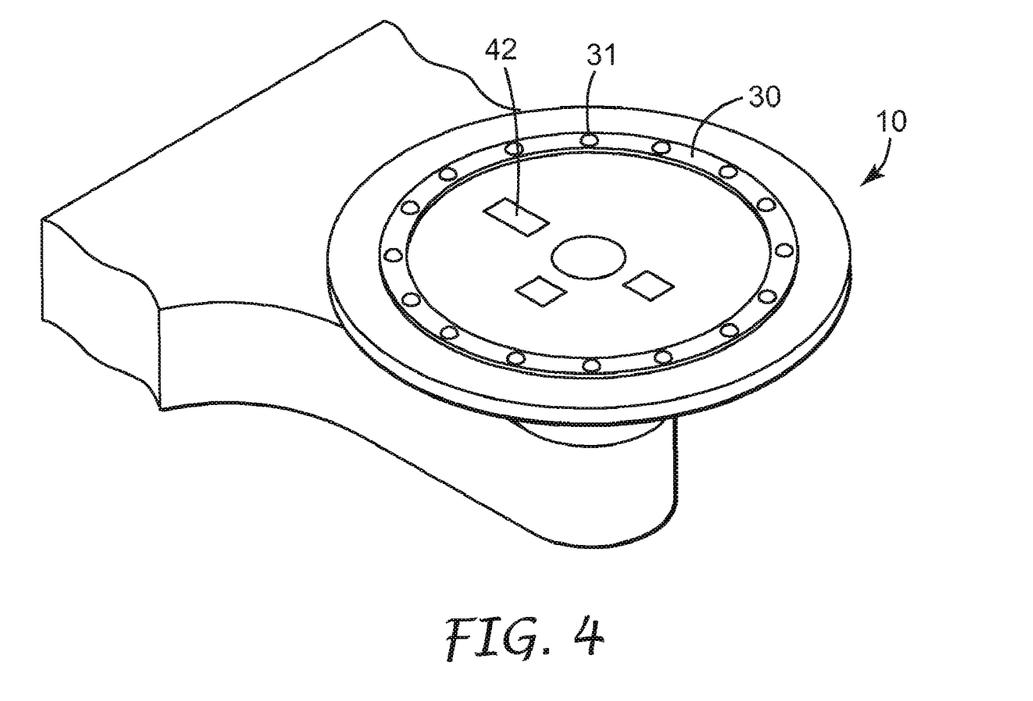
FIG. 4 is a top perspective view of the base plate of the sample processing system of FIG. 1, with the base plate removed from the system.

FIG. 4 is a top perspective view of the base plate 10 separated from the drive system 20. Separation of the base plate 10 from the drive system 20 allows for viewing of the connection apparatus used to connect the base plate 10 to the shaft 22 while at the same time making any required connections to the devices (e.g., the temperature sensors 42 and 44 seen in FIG. 3) on the base plate 10. The connection apparatus in the embodiment depicted in FIGS. 2 and 4 includes a base plate connector 52 that is preferably fixedly attached to the base plate 10 and a drive side connector 54 (see FIG. 1) that is fixedly attached to the shaft 22. The connectors 52 and 54 provide electrical connections between devices on the base plate 10 and the remainder of the sample processing system.

As used in connection with the present invention, the term "fixedly" means that the base plate side connector 52 is attached to the base plate 10 in a manner that requires removal of some fastening structure (e.g., removal of a threaded fastener, retaining brackets, etc.) or destruction of some fastening material (e.g., adhesive, epoxy, solder, etc.) to separate the base plate side connector 52 from the base plate 10. In some instances, the base plate side connector 52 may be integrally molded with at least a portion of the base plate 10.

In the depicted embodiment, the electrical connections between the base plate side connector 52 and the drive side connector 54 (see FIG. 1) are made through pins 53 located on the base plate side connector 52 (see FIG. 2). The pins 53 mate with sockets 55 (see FIG. 1) provided on the drive side connector 54. It will be understood that the pins and sockets used in the depicted embodiment may be replaced by any number of alternative structures capable of making the required electrical connections.

Furthermore, although the depicted connectors 52 and 54 (see FIG. 1) make only electrical connections for power and/ or data transmission between the base plate 10 and the remainder of the system, it will be understood that the connectors could also make many other connections such as, e.g., optical connections, fluid connections, etc.

Any connections made between the base plate 10 and the remainder of the system should take rotation of the base plate 10 into consideration. Where the connections made through base plate side connector 52 and the drive side connector 54 (see FIG. 1) are electrical in nature, they may preferably be made through a rotary connector on which the drive side connector 54 rotates with the shaft 22. Suitable slip ring connectors may be obtained from, e.g., Litton Poly-Scientific (Blacksburg, Va.). Other rotary connectors such as mercury contacts are available from, e.g., Meridian Laboratory (Middleton, Wis.). The specific selection of a rotary connector will be based on a variety of factors such as the number of connections to be made, rotational speed required, power handling limits, etc.

Together, the base plate side connector 52 and the drive side connector 54 (see FIG. 1) provide one embodiment of a "connection apparatus" useful in connecting the base plate 10 to the remainder of the sample processing system. The connection apparatus is used to releasably attach the base plate to the remainder of the system.

As used in connection with the present invention, "releasably attach" (and variations thereof) means that the connection apparatus provides a connection that can be separated or taken apart without destruction of either the base plate or the system. In other words, a connection apparatus that provides releasable attachment of the base plate 10 to the system can be reused such that the base plate 10 can be detached and reattached without destruction of the connection apparatus. Advantages of such a connection apparatus are the ability to easily and rapidly remove a base plate from the system for replacement due to malfunctioning components or, more probable, due to the need for a base plate having a different configuration.

In addition to making connections that transmit power and/or signals between the base plate 10 and the reminder of the sample processing system, the connection apparatus (of the base plate side connector 52 and the drive side connector 54) may also provide other functions. For example, the pins and sockets may also provide some mechanical structure that provides identification of the base plate 10 to the remainder of the system. In other words, the pattern of the pins and the connections made between the pins and sockets within the connection apparatus may uniquely identify different types of base plates to the system. Alternatively, pins and sockets or other mechanical structures may be relied on to identify each base plate to the system.

Optionally, identification of the base plates by the sample processing systems may be made by other techniques, e.g., optical markers, patterns, bar codes, etc. Returning to FIG. 2, for example, the base plate 10 may include indicia 18 such as, e.g., a bar code, that can be read by the system to identify a specific base plate or a type of base plate. In another alternative, the base plates may be identified to the system by, e.g., the use of a Radio Frequency Identification (RFID) tag device embedded in or attached to the base plate 10.

Figure 4A:
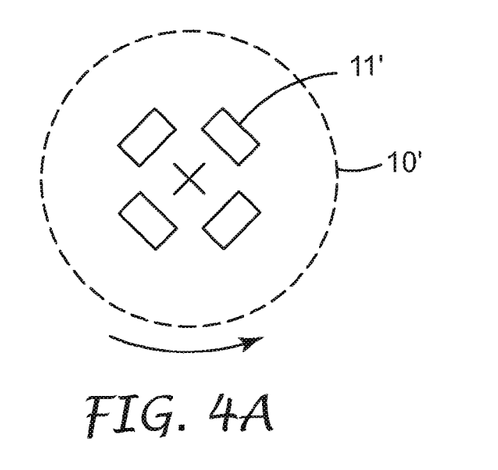
FIG. 4A is a schematic diagram of an alternative system in which the base plate includes coils to generate electricity as the base plate rotates.

FIG. 4A is a schematic depiction of a portion of an alternative system according to the principles of the present invention. In some instances, it may be difficult to provide sufficient electrical power to operate devices mounted on the base plates through a rotating connection apparatus such as those described above. An alternative manner in which electrical power may be supplied relies on the rotation of the base plate 10'. A magnetic field may be provided in the system through which the base plate 10' rotates.

One or more generator coils 11' may be operatively attached to the base plate (e.g., located on or within the base plate 10') such that as the base plate 10' rotates in the direction of the depicted arrow, the generator coils 11' pass through the provided magnetic field. As the generator coils 11' pass through the magnetic field electrical energy is generated to operate any electrically powered devices supplied on the base plate 10'.

Although some signal connections may still be made through a connection apparatus as described above, it may be possible to provide for all communication of information into and out of devices on the base plate 10' by non-contact techniques (e.g., optical, RF, etc.) such that the connection apparatus connecting the base plate 10' and the drive system is purely mechanical, providing only a coupling capable of rotating the base plate 10' as desired.

Figure 5:
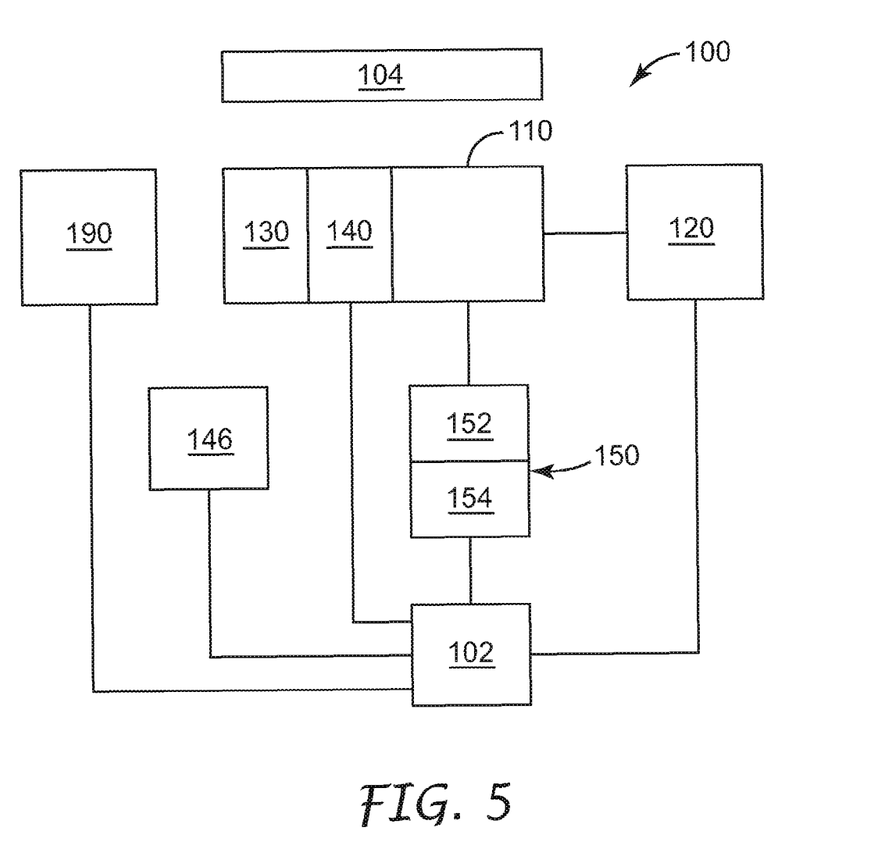
FIG. 5 is a schematic block diagram of one sample processing system according to the present invention.

FIG. 5 is a schematic block diagram of one illustrative example of a sample processing system 100 according to the present invention. The system 100 includes a base plate 110 with thermal structure 130 incorporated therein. Although not a part of the sample processing system 100, a sample processing device 104 is depicted in FIG. 5 and may be located on the base plate 110 in contact with the thermal structure 130. Although the thermal structure 130 is depicted as a single component in system 100, it should be understood that the system may, optionally include one, two, three, or more individual thermal structures incorporated into the base plate 110.

The base plate 110 is operably attached to drive system 120 for rotation. The drive system 120 is controlled by the system controller 102 and may be used for positioning the base plate 110 in a desired rotational orientation, controlling the rotational speed of the base plate 110, controlling the acceleration and/or deceleration profiles of the base plate 110, etc.

The base plate 110 also includes a temperature sensor 140 that is in communication with a system controller 102. The temperature sensor 140 is preferably capable of providing a signal to system controller 102 that is indicative of the temperature of the thermal structure 130. That communication may involve only a signal from a single device located in thermal communication with the thermal structure 130. Alternatively, the temperature sensor 140 may include one or more sensors in thermal communication with the thermal structure 130 and one or more reference sensors in thermal communication with the remainder of the base plate 110.

As used in connection with the present invention, "communication" between the system components, e.g., the temperature sensor 140 and system controller 102, may be achieved by any suitable technique and/or mechanisms. The communication may be in the form of electrical signals passing through wires or circuits, radio or telemetry based communication, optical communication through fiber optics or via remote transmitters and receivers, etc. The indication of communication by lines in the figures should be indicative of a communication link only, not a requirement for physical connection via, e.g., wires or fiber optic cables.

The temperature sensor 140 is in communication with the system controller 102. That communication may be established by any suitable technique, e.g., electrical, optical, digital, analog, radio, etc. In the illustrated embodiment, communication from the temperature sensor 140 to the system controller 102 is routed through a connection apparatus 150 that includes a base plate side connector 152 and a drive side connector 154.

An optional remote temperature sensor 146 is depicted in FIG. 5 and is also in communication with the system controller 102. That communication may be established by any suitable technique, e.g., electrical, optical, digital, analog, radio, etc. The remote temperature sensor 146 may be provided to monitor the temperature of any portion or portions of the base plate 110, thermal structure 130 or a sample processing device 104 located on the base plate 110. Although the remote temperature sensor 146 is depicted as a single component in system 100, it should be understood that it may, optionally include one, two, three, or more individual devices.

In addition, the sample processing system 100 also includes an electromagnetic energy source 190 in communication with the system controller 102. As discussed above, the electromagnetic energy source 190 preferably directs electromagnetic energy at the thermal structure 130 where it is absorbed and converted to thermal energy. Although the electromagnetic energy source 190 is depicted as a single component in system 100, it should be understood that the system 100 may, optionally include one, two, three, or more individual devices that make up the electromagnetic energy source 190.

In use, the sample processing system 100 may operate in methods in which, after locating a sample processing device 104 on the base plate 110, the base plate 110 is rotated by the drive system 120. The speed of rotation provided by the drive system 120 is controlled by the system controller 102, which is connected to the drive system 120 by any suitable technique. As the base plate 110 rotates, the system controller 102 preferably directs the electromagnetic energy source 190 to direct electromagnetic energy at the thermal structure 130, where that electromagnetic energy can be absorbed and converted to thermal energy for transmission to the sample processing device 104 located on the base plate 110.

As the thermal structure 130 is heated, the temperature sensor 140 on the base plate and/or the remote temperature sensor 146 may provide signals to the system controller 102. Those signals may be used to control the temperature of the thermal structure 130 by controlling the rotational speed of the drive system 120 and/or controlling the electromagnetic energy delivered by the electromagnetic energy source 190 to the thermal structure 130. Control over the delivery of electromagnetic energy to the thermal structure 130 from the source 190 may be accomplished in a variety of techniques, e.g., controlling the intensity of the energy emitted by the source 190, shuttering the electromagnetic energy, pulsing or cycling the electromagnetic energy source 190, etc.

Figure 6:
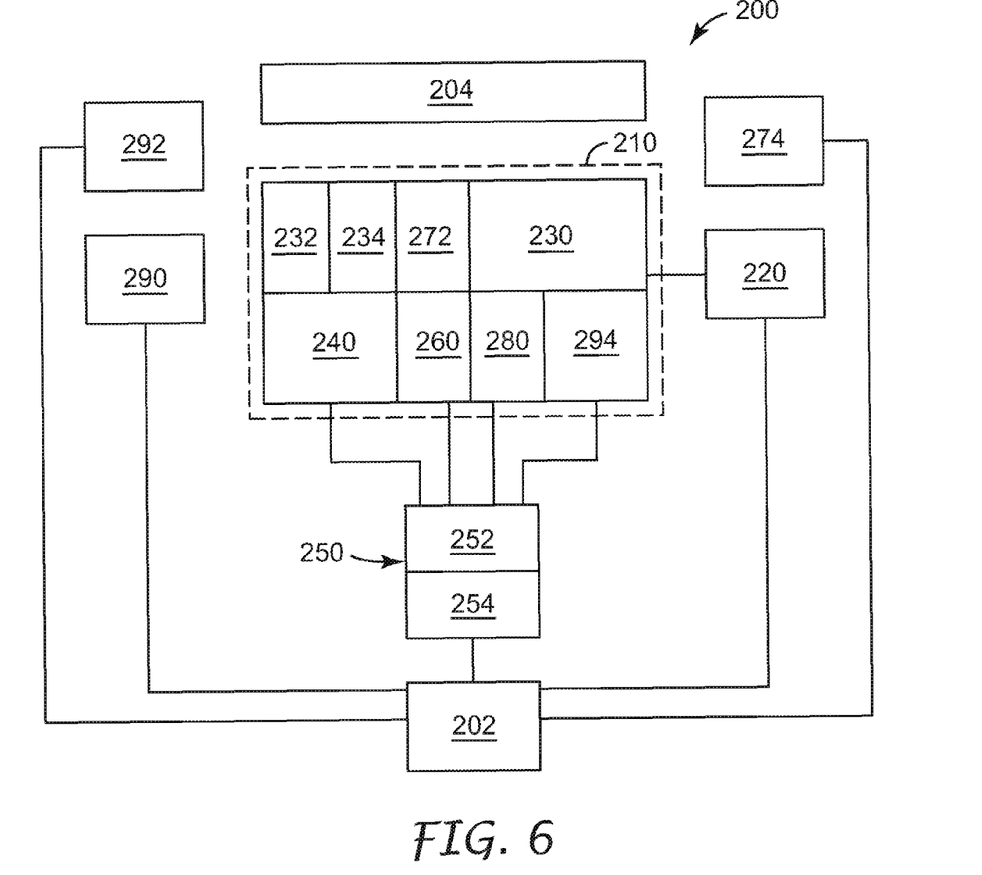
FIG. 6 is a schematic block diagram of another sample processing system according to the present invention.

Turning now to FIG. 6, an alternative sample processing system 200 is depicted in a schematic block diagram. The system 200 includes a base plate 210 with thermal structure 230 incorporated therein. A sample processing device 204 is depicted in FIG. 6 located on the base plate 210 in contact with thermal structures 232 and 234. It should be understood, however, that the sample processing device 204 does not form a part of the sample processing system 200.

The base plate 210 is operably attached to drive system 220 for rotation. The drive system 220 is controlled by the system controller 202 and may be used for positioning the base plate 210 in a desired rotational orientation, controlling the rotational speed of the base plate 210, controlling the acceleration and/or deceleration profiles of the base plate 210, etc.

The system 200 also includes a temperature sensor 240 that is connected to a system controller 202. The temperature sensor 240 is preferably capable of providing a signal to system controller 202 that is indicative of the temperature of one or both of the thermal structure 232 and 234. That communication may involve only a signal from a single device located in thermal communication with each of the thermal structures 232 and 234. Alternatively, the temperature sensor 240 may include one or more sensors in thermal communication with each of the thermal structures 232 and 234 and one or more reference sensors in thermal communication with the remainder of the base plate 210.

The temperature sensor 240 is in communication with the system controller 202. That communication may be established by any suitable technique, e.g., electrical, optical, digital, analog, radio, etc. In the illustrated embodiment, communication from the temperature sensor 240 to the system controller 202 is routed through a connection apparatus 250 that includes a base plate side connector 252 and a drive side connector 254.

FIG. 6 also depicts an optional microprocessor 260 located on the base plate 210 that is also in communication with the system controller 202. That communication may be established by any suitable technique, e.g., electrical, optical, digital, analog, radio, etc. The microprocessor 260 may also preferably receive power from the system controller 202 to support its operation. Both the communication link and the power are preferably routed through the connection apparatus 250.

The microprocessor 260 may perform a variety of functions. For example the microprocessor 260 may receive a signal from the temperature sensor 240 and route that signal to the system controller 202 (in which case the link between the temperature sensor 240 and the system controller 202 may be solely to provide power to the temperature sensor 240). The microprocessor 260 may perform some processing of the signal received from the temperature sensor 240 or it may simply pass the data to the system controller 202.

Also depicted in FIG. 6 is an optional detection component 272 mounted on the base plate 210 which may, e.g., be provided as a photodetector to detect emission of, e.g., some electromagnetic energy from the sample processing device 204. If such a detection component 272 is provided, it may preferably be in communication with the microprocessor 260 as depicted in FIG. 6. Alternatively, the detection component 272 may be in direct communication with the system controller 202, particularly if no microprocessor 260 is provided on the base plate 210.

In addition, system 200 also includes an optional remote detection system 274 that is not located on the base plate 210. The remote detection system 274 may be used to detect emissions from the sample processing device 204 during sample processing. The remote detection system 274 may be passive or active (e.g., it may actively interrogate process chambers in the sample processing device 204). The remote detection system 274 is preferably in communication with the system controller 202 which may receive signals from and/or control operation of the remote detection system 274.

The system 200 also includes an optional light source 280 located on the base plate 210 that may to used to, e.g., supply light to the sample processing device 204. The light source 280 may be in the form of an LED or other light emitting construction. Further, the light source may be directly linked to the system controller 202 (through the connection apparatus 250) for power and control. Alternatively, the microprocessor 260 on base plate 210 may be used to control operation of the light source 280.

The sample processing system 200 also includes an electromagnetic energy source 290 in communication with the system controller 202. As discussed above, the electromagnetic energy source 290 preferably directs electromagnetic energy at the thermal structures 232 and 234 where it is absorbed and converted to thermal energy. The source 290 may be capable of delivering electromagnetic energy to only one of the thermal structures at a time or it may be capable of delivering electromagnetic energy to both thermal structures at the same time. Although the electromagnetic energy source 290 is depicted as a single component in system 200, it should be understood that the system 200 may, optionally include one, two, three, or more individual devices that make up the electromagnetic energy source 290.

The system 200 also includes an optional sample device electromagnetic energy source 292 that is preferably arranged to deliver electromagnetic energy directly to a sample processing device 204 (in contrast to delivering electromagnetic energy to the thermal structures 232 and 234 as source 290 does). The sample device electromagnetic energy source 292 may preferably be controlled by the system controller 202 as depicted in FIG. 6. Operation of a sample device electromagnetic energy source 292 is described more completely below in connection with FIG. 7.

Another optional feature of sample processing systems of the present invention is also depicted in FIG. 6 in the form of a thermal control element 294 located on the base plate 210. The thermal control element 294 is depicted as being communication with the system controller 202 through connection apparatus 250, although thermal control element 294 may only receive power through that connection, with control signals optionally being provided by the base plate controller 260.

The thermal control element 294 may preferably be provided in connection with one or both of the thermal structures 232 and 234 and may be used to assist in controlling the temperature of the thermal structures 232 and 234. Alternatively or in addition to controlling the temperature of the thermal structures 232 and 234, the thermal control element 294 may be used to control the temperature of the remainder of the base plate 210. The thermal control element 294 may take a variety of forms, e.g., electrical resistance heaters, thermoelectric modules (e.g., Peltier elements) etc. Furthermore, although the thermal control element 294 is depicted as a single component in system 200, it should be understood that the system 200 may, optionally include one, two, three, or more individual devices that collectively make up the thermal control element 294. In addition, the thermal control element 294, if provided in the form of multiple devices, may be composed of the same type of device or a collection of different types of devices (e.g., resistance heaters in combination with Peltier elements).

In use, the sample processing system 200 may operate in methods in which, after locating a sample processing device 204 on the base plate 210, the base plate 210 is rotated by the drive system 220. The speed of rotation provided by the drive system 220 is controlled by the system controller 202, which is connected to the drive system 220 by any suitable technique. As the base plate 210 rotates, the system controller 202 preferably directs the electromagnetic energy source 290 to direct electromagnetic energy at one or both of the thermal structures 232 and 234, where that electromagnetic energy can be absorbed and converted to thermal energy for transmission to the sample processing device 204 located on the base plate 210.

As the thermal structure 230 is heated, the temperature sensor 240 may provide signals to the system controller 202 directly or through the microprocessor 260. Those signals may be used to control the temperature of the thermal structures 232 and 234 by controlling the rotational speed of the drive system 220 and/or controlling the electromagnetic energy delivered by the electromagnetic energy source 290 to the thermal structures 232 and 234. Control over the amount of electromagnetic energy delivered to the thermal structures 232 and 234 from the source 290 may be accomplished in a variety of techniques, e.g., controlling the intensity of the energy emitted by the source 290, shuttering the electromagnetic energy, pulsing or cycling the electromagnetic energy source 290, etc.

In addition, operation of the system 200 may include the use of the photodetector 272, light source 280, remote detection system 274, sample device electromagnetic energy source 292, and/or thermal control element 294 as described above.

Figure 7:
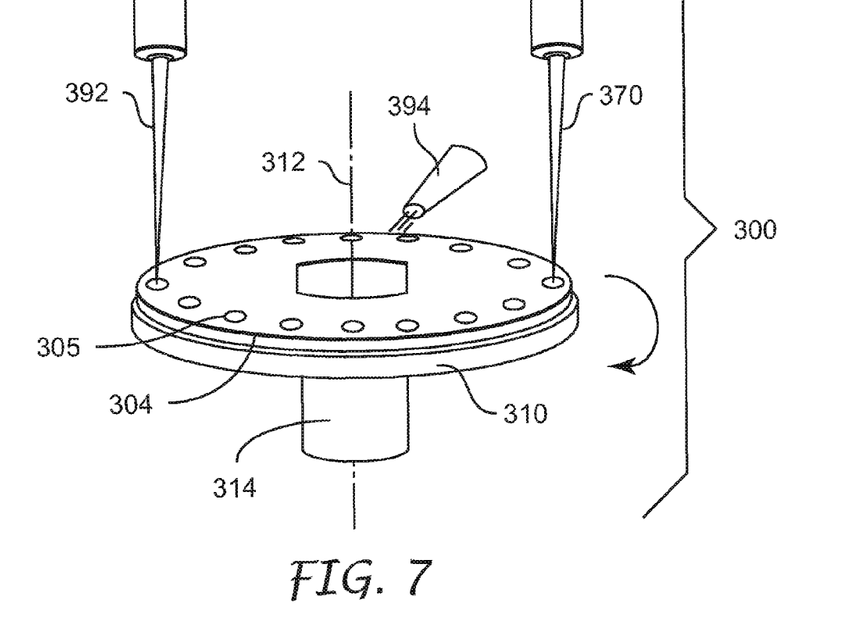
FIG. 7 depicts a portion of an alternative sample processing system according to the present invention.

FIG. 7 depicts a portion of an alternative sample processing system 300 with a sample processing device 304 located on a base plate 310 that rotates the sample processing device 304 about an axis 312. The sample processing device 304 includes process chambers 305 that preferably contain sample material.

The system 300 includes an electromagnetic energy source 392 directing electromagnetic energy directed at the sample chambers 305 to heat the sample materials contained therein (unlike the electromagnetic energy source 90 in the system of FIGS. 1-3 in which the electromagnetic energy is directed at the thermal structure on the base plate). The electromagnetic energy source 392 is preferably remote from the sample processing device 304 and the base plate 310. Examples of some suitable electromagnetic energy sources may include, but are not limited to, lasers, broadband electromagnetic energy sources (e.g., white light), etc. The electromagnetic energy source 392 may provide electromagnetic energy continuously or intermittently based on a variety of factors, e.g., the desired temperature of the sample materials, the rate at which thermal energy is removed from each process chamber, the desired rate of temperature change, whether the process chambers include a reflective component, etc. If the electromagnetic energy source 392 is cycled or otherwise varied, a registration system may be used to deliver a selected amount of electromagnetic energy to selected process chambers 305 on the sample processing device 304.

The sample processing system 300 depicted in FIG. 7 also includes an optional additional temperature control mechanism in the form of a fluid source 394, e.g., pressurized air or any other suitable fluid, that can be directed at the surface of the sample processing device 304. The fluid used can be either heated or cooled to a desired temperature. Where it is desired to cycle the sample materials between upper and lower temperatures, the fluid may be provided at the lower temperature. Although depicted as being directed at only one surface of the sample processing device 304, it will be understood that the fluid may be directed at both surfaces of the device 304 if both surfaces are exposed.

The system 300 may also include various other components such as a remote detection system 370 provided to detect the results of processing of the sample materials in the process chambers 305 of the sample processing device 304. For example, the detection system and method may involve active interrogation of the process chambers 305 to detect fluorescent reaction products in the chambers as the device 304 rotates. The detection may be qualitative or quantitative. Other detection systems may be provided to monitor, e.g., the temperatures or other properties of the materials in the process chambers 305 on the sample processing device 304.

Although not shown in FIG. 7, it will be understood that the base plate 310 may also include one or more thermal structures such as those discussed above in connection with base plate 10. The system 300 may also then include an electromagnetic energy source arranged to deliver electromagnetic energy to the thermal structure, also as discussed above. That electromagnetic energy source may be separate from the source 392 delivering electromagnetic energy to the sample processing device 304, or it may be the same source—with the energy emitted by the source 392 being divided to reach both the sample processing device 304 and the thermal structure or structures in the base plate 310. Any method of sample processing using such a system, i.e., a system in which electromagnetic energy can be delivered to both the sample processing device 304 and any thermal structures in the base plate 310 on which the sample processing device 304 is located, may involve sequential or simultaneous delivery of electromagnetic energy to both the process chambers 305 and the thermal structure as desired.

Figure 8:
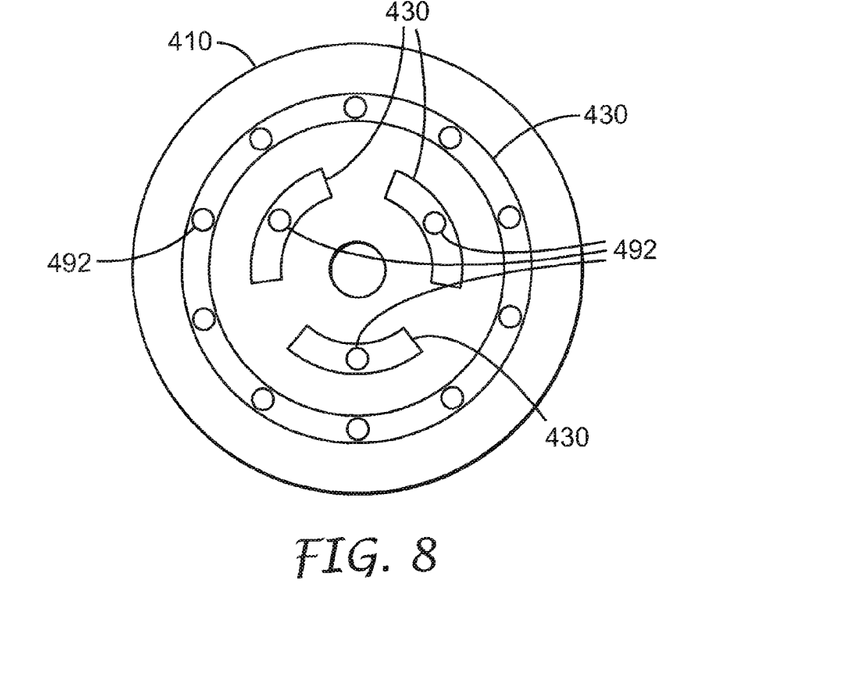
FIG. 8 depicts another embodiment of a base plate that may be used in connection with sample processing systems according to the present invention.

FIG. 8 depicts another embodiment of a base plate 410 that may be used in connection with the present invention, in which the base plate 410 includes a number of independent thermal structures 430. Each of the thermal structures 430 includes at least one thermoelectric module 492 attached thereto or embedded therein to assist in controlling the temperature of the thermal structures 430. Some of the thermal structures 430 include only one thermoelectric module 492 and others include two or more thermoelectric modules 492. Such a base plate incorporating thermoelectric modules may be used in connection with, e.g., a sample processing system such as that depicted and described in connection with FIG. 6.

With the base plate 410, control over the temperature of the thermal structures 430 may be effected by controlling the temperature of the thermoelectric modules 492 alone or in combination with electromagnetic energy directed at the bottom surface of the thermal structures 430 (if the bottom surfaces are exposed as depicted in the embodiment of FIGS. 1-3. Where the temperature of the thermal structures 430 is to be controlled by controlling the temperature of the thermoelectric modules 492 alone (i.e., where the thermal structures 430 are not to be heated by converting electromagnetic energy directed at the thermal structures 430 to thermal energy), the materials selected for manufacturing the thermal structures 430 may be chosen based on their thermal conductivity, with no consideration given for the ability of the materials to absorb electromagnetic energy. Suitable materials may include but are not limited to, e.g., metals (such as, e.g., aluminum, gold, copper, etc.).

By combining the thermoelectric modules 492 with thermal structures 430, advantages may be obtained in the form of improved temperature uniformity as the thermal structures 430 serve as sinks to equilibrate variations in the operating characteristics of the individual thermoelectric modules 492.

The thermoelectric modules 492 provide another option in controlling the temperature of sample materials in the process chambers of sample processing device located on the base plate 410. The thermoelectric modules 492 may be used in addition to directing electromagnetic energy into the process chambers and/or directing electromagnetic energy at the thermal structures 430 themselves to provide three potential thermal energy sources. Alternatively, the thermoelectric modules 492 may be used alone to heat the process chambers on a sample processing device located on the base plate 410 or they may be used in connection with the delivery of electromagnetic energy directly into the process chambers of the device (in the absence of electromagnetic energy directed at the bottom surface of the thermal structures 430).

The net result may be a system having the ability to provide electromagnetic energy directly into the process chambers, thermal structures that can convert impinging electromagnetic energy into thermal energy for conduction to the process chambers in a device, and thermoelectric modules whose temperature can be controlled to control the temperature of the thermal structures (and, in turn, any process chambers in thermal communication with the thermal structures). As a result, temperature control over sample materials within the process chambers of a sample processing device located on the base plate may be effected in a variety of manners.

Figure 9:
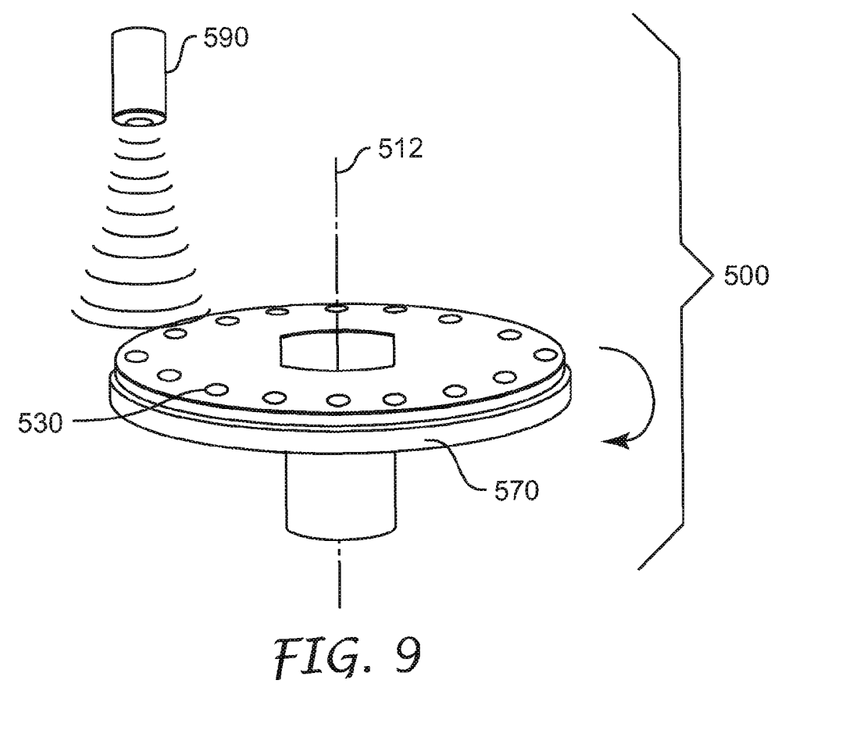
FIG. 9 depicts a portion of another sample processing system according to the present invention

FIG. 9 schematically illustrates a portion of another sample processing system 500 including a base plate 510 that rotates about an axis 512. The base plate 510 includes thermal structures 530 that can be selectively heated by suitable electromagnetic energy, e.g., RF, microwave, etc., supplied by an electromagnetic energy source 590 to heat electromagnetic energy receptive materials in the thermal structure 530. The electromagnetic energy receptive materials can then communicate the thermal energy to a sample processing device located on the base plate 510. The electromagnetic energy source 570 may provide electromagnetic energy continuously or intermittently as discussed above.

In such a sample processing system, it may be preferred that the remainder of the base plate 510 (outside of the thermal structures 530) be substantially transmissive for the electromagnetic energy delivered by source 590. It may also be preferred that the materials used for the remainder of the base plate 510 have relatively low thermal conductivity and relatively low thermal mass.

Figure 10:
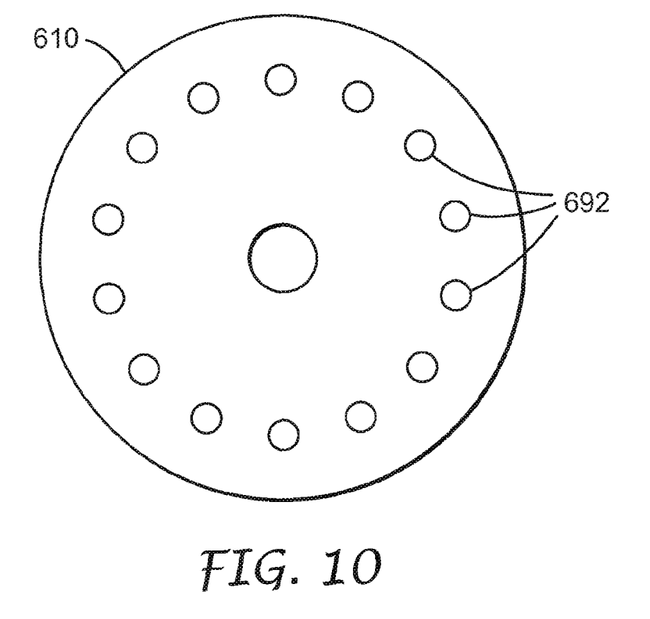
FIG. 10 depicts another embodiment of a base plate that may be used in connection with sample processing systems according to the present invention.

FIG. 10 depicts another alternative base plate design in which a number of thermoelectric modules 692 are located directly within a base plate 610, i.e., in the absence of any thermal structure as discussed above in connection with FIG. 8. It may be desired that the thermoelectric modules 692 protrude above the surrounding surface of the base plate 610 (in a manner similar to the raised protrusions 31 of thermal structure 30 as described in connection with the embodiment of FIGS. 1-3). The size and location of the protruding thermoelectric modules may preferably be selected to correspond to the size and location of any process chambers on a sample processing device to be located on the base plate 610.

The protruding thermoelectric modules 692 may enhance thermal transfer between the process chambers and base plate 610 in a number of ways. For example, if the protruding thermoelectric modules 692 extend at least partially into the process chambers of the sample processing device, they can increase the surface area of the process chamber that is exposed to the protruding thermoelectric modules 692. In addition, by affirmatively engaging any process chambers, the protruding thermoelectric modules 692 may reduce or eliminate any air gaps between the process chambers and the protruding thermoelectric modules 692 in the area of the process chambers. Such air gaps may insulate the process chambers from the thermoelectric modules 692, thereby degrading thermal transfer.

In a manner similar to that discussed with respect to the thermal structures depicted in FIG. 3 above, the thermoelectric modules 692 may extend above the surface of the base plate 610 such that the thermoelectric modules 692 support any sample processing device mounted on the base plate 610, such that the sample processing device does not contact the surface of the base plate 610 that surrounds the thermoelectric modules 692.

Further, it may be desirable to supply a force on a sample processing device to urge the sample processing device and base plate 610 towards each other. In some embodiments, such a force may be provided by a platen urging the sample processing device against the base plate 610. In other embodiments, the sample processing device may be drawn towards the base plate 610 by, e.g., a spindle that extends through a central opening in the sample processing device and draws the sample processing device towards base plate 610. Other structures and/or mechanisms for providing a force urging a sample processing device and base plate 610 together will be known to those skilled in the art.

It is to be understood that the above description is intended to be illustrative, and not restrictive. Various modifications and alterations of this invention will become apparent to those skilled in the art from the foregoing description without departing from the scope of this invention, and it should be understood that this invention is not to be unduly limited to the illustrative embodiments set forth herein.

The invention claimed is:

1. A sample processing system comprising:
a base plate adapted to receive a sample processing device proximate a top surface of the base plate;
a thermal structure exposed on the top surface of the base plate, wherein an upper surface of the thermal structure contacts a sample processing device received proximate the top surface of the base plate, wherein the upper surface of the thermal structure includes a non-planar surface that is raised relative to the top surface of the base plate adjacent the thermal structure, and wherein the thermal structure includes at least one of a thermoelectric module and an electrical resistance heater; and
a drive system adapted to rotate the base plate about an axis of rotation.

2. The sample processing system of claim 1, further comprising an electromagnetic energy source adapted to direct electromagnetic energy at the thermal structure while the base plate is rotating about the axis of rotation.

3. The sample processing system of claim 2, wherein the thermal structure is opaque to the electromagnetic energy emitted by the electromagnetic energy source.

4. The sample processing system of claim 1, wherein the thermal structure is positioned to extend at least partially into a process chamber of the sample processing device when the sample processing device is received proximate a top surface of the base plate.

5. The sample processing system of claim 1, wherein the thermal structure is positioned to minimize any air gaps between a process chamber of the sample processing device and the thermal structure.

6. The sample processing system of claim 1, wherein the thermal structure is positioned to support the sample processing device, such that the sample processing device does not contact the top surface of the base plate that surrounds the thermal structure when the sample processing device is received proximate a top surface of the base plate.

7. The sample processing system of claim 1, wherein the thermal structure is one of a plurality of thermal structures attached to the base plate.

8. The sample processing system of claim 1, wherein the thermal structure consists of at least one of a thermoelectric module and an electrical resistance heater.

9. The sample processing system of claim 1, wherein the non-planar upper surface of the thermal structure comprises a raised protrusion extending upward from surrounding portions of the upper surface.

* * * * *